United States Patent [19]
Vaillancourt

[11] Patent Number: 5,487,728
[45] Date of Patent: Jan. 30, 1996

[54] CONNECTOR ASSEMBLY

[76] Inventor: Vincent L. Vaillancourt, 14 Bunyan Dr., Livingston, N.J. 07039

[21] Appl. No.: 245,893

[22] Filed: May 19, 1994

[51] Int. Cl.[6] .................................................. A61M 5/00
[52] U.S. Cl. ........................... 604/86; 604/167; 604/244; 604/201
[58] Field of Search ............................ 604/86, 201, 205, 604/280, 283, 905, 167, 411, 414, 192, 198, 244

[56] References Cited

U.S. PATENT DOCUMENTS

| | | | |
|---|---|---|---|
| 4,294,249 | 10/1981 | Sheehan et al. | 604/86 |
| 4,981,469 | 1/1991 | Whitehouse et al. | 604/86 |
| 5,122,123 | 6/1992 | Vaillancourt | 604/905 X |
| 5,295,657 | 3/1994 | Atkinson | 604/167 X |

*Primary Examiner*—John D. Yasko
*Attorney, Agent, or Firm*—McAulay, Fisher, Nissen, Goldberg & Kiel

[57] ABSTRACT

The connector assembly includes a female luer connector having a hollow needle disposed in recessed position within a rigid tubular portion. A rubber shield having a tubular portion and a septum at one end is positioned over the needle to maintain the needle in a sealed condition. A compression ring is disposed about the rubber septum to hold the septum in compression whereby the punctured area can be punctured many times without leaking when subjected to relatively high pressures. The male connector may be of any suitable type for pushing the rubber septum into the female connector for piercing by the needle of the female connector.

20 Claims, 1 Drawing Sheet

CONNECTOR ASSEMBLY

This invention relates to a connector assembly. More specifically, this invention relates to a connector assembly for medical uses.

As is known, various types of connector assemblies have been known for connecting various types of medical components together. In some cases, the connector assemblies have been constructed to effect a rapid connection and disconnection between two lines for conveying fluids to a patient. In other cases, connector assemblies have been constructed to maintain a needle in a sterile connector, for example, where a syringe or a like structure is to be connected to a catheter or the like for the infusion of a medicant into a patient or for removal of blood from a patient. Still, in other cases, connector assemblies have been constructed to protect against a needle stick from a needle employed in a medical component or instrument which is to be connected to another medical component.

By way of example, U.S. Pat. No. 5, 122, 123 describes a closed system connector assembly formed between a female connector in which a hollow needle is mounted and a male connector. As described, the needle is maintained in a protected fashion by means of a collapsible tube, for example, one made of rubber and disposed about the needle, and a septum at the end of the collapsible tube. In addition, the male connector carries a membrane at one end to seal off the lumen of the male connector. Insertion of the male connector into the female connector causes the tube to collapse in accordion fashion while the hollow needle pierces not only the membrane of the female connector but also the septum of the male connector. Upon withdrawal of the male connector, the collapsible tube within the female connector springs forwardly causing the membrane to again take up a position closing off the needle from the outside environment.

U.S. Pat. No. 5,290,254 describes a shielded cannula assembly which can be mounted on a syringe and which houses a hollow needle within a collapsible tubular shield having a cap at a distal end which can be pierced by the needle when the shield is collapsed. Additional embodiments are described where the shielded cannula assembly can be used as a hypodermic needle assembly to withdraw a fluid from a vial and as a cannula assembly for use in collecting blood or as a transfer needle assembly.

U.S. Pat. No. 4,998,927 describes a connector assembly in which a hollow needle is encased in a housing and covered over by a rubber septum which is mounted on a collapsible means which permits the needle to pierce through the septum into communication with another chamber. A major attribute of this assembly is that the rubber septum can be relatively thick, for example from 0.150 inches to 0.250 inches, thereby assuring a seal each time even though the septum may be pierced twenty five or more times. A disadvantage, however, is that in the embodiments where a female connector houses the rubber septum, the female connector may become a trap for bacteria between uses of the connector assembly.

It is also known that where a needle pierces through a rubber septum multiple times that a coring effect may occur in which a leakage path is formed through the rubber septum when the septum is in an extended position relative to the hollow needle. In such cases, if fluid is contained within the connector in which the hollow needle is mounted, leakage of the fluid may occur, particularly, if the fluid is under pressure. Accordingly, the usable life of such connectors can be relatively limited.

It is also known that where a rubber septum is of a restricted thickness and diameter, for example, of a thickness in the range of 0.100 inches, the septum may only take a few punctures before fluid pressure from a patient or IV line pump causes leakage.

Accordingly, it is an object of the invention to reduce the risk of leakage from a shielded connector employing a hollow needle.

It is another object of the invention to provide a connector assembly employing a male luer connector and a female luer connector which can experience multiple connections and disconnections without leakage of a shielded hollow needle in the female luer connector.

It is another object of the invention to reduce the risk of leakage from a shielded connector employed within a restricted space.

It is another object of the invention to enable a rubber septum of a connector assembly to accept many punctures without leakage.

Briefly, the invention provides a connector assembly which comprises two connectors which can be coupled and uncoupled together in a rapid and simple manner.

One connector, for example in the form of a female luer connector, includes a rigid tubular portion, a hollow needle fixedly mounted within the tubular portion, a resilient collapsible tubular portion concentrically between the needle and the rigid tubular portion and a cap-shaped septum at a distal end of the collapsible tubular portion for movement between an extended position with a face of the septum at a distal end of the rigid tubular portion and a recessed position within the rigid tubular portion. As such, the connector is constructed in similar fashion to the female connector described in U.S. Pat. No. 5,122,123. In addition, this connector includes a ring which is disposed circumferentially of the septum to prevent circumferential distortion of the septum.

The second connector acts as a means for moving the septum of the first connector from the extended position to the recessed position in order to effect piercing of the needle through the septum while resiliently collapsing the collapsible tubular portion. In this regard, the second connector includes a hollow tube for projecting into the rigid tubular portion of the first connector. This tube is further provided with a lumen and is sized to push the septum into the rigid tubular portion to effect piercing of the needle through the septum into the lumen of the hollow tube.

The second connector may be made in the form of a male luer slip, a needle with a shield about the needle, a tubing adaptor, for example, in the form of a molded plastic element in the shape of a tube to which plastic tubing can be secured, and the like.

The ring which is provided on the septum of the first connector may be made of a plastic material which is sufficiently rigid to prevent circumferential distortion of the septum during piercing of a hollow needle through the septum. Preferably, the ring is made of an engineering plastic such as Nylon, acetal or the like. The ring imposes a sufficient circumferential compressive force on the septum so as to close the opening formed in the septum due to the passage of the needle therethrough. In this respect, it has been found that a septum made of silicone rubber placed under an initial compression of from 5% to 10% of its outer diameter and made of a thickness of 0.050 inches may be pierced over twenty five times with no leakage once subjected to 30 psig air pressure. On the other hand, if made of Latex rubber, the septum requires a larger thickness, for example up to 0.100 inches maximum for the same compression in order to allow multiple punctures.

The ring may be of any suitable cross-sectional shape, such as a flat rectangular shape, and may be hidden from view by being recessed within the septum so that only the front face of the septum is exposed to view.

The connector may also be provided with means for releasably coupling the two connectors together with the hollow tube of one connector within the rigid tubular portion of the other connector. Such a means may include a housing on the second connector having an internal thread and a pair of radially directed projections on the rigid tubular portion of the first connector for threading into the internal thread.

These and other objects and advantages of the invention will become more apparent from the following detailed description taken in conjunction with the accompanying drawings wherein.

Figure 1:
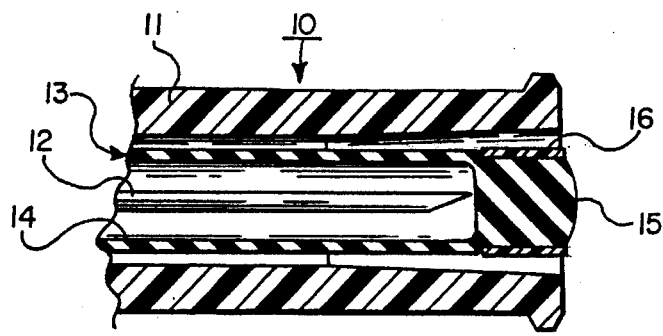
FIG. 1 illustrates a part cross sectional view of a female luer connector constructed in accordance with the invention.

Referring to FIG. 1, the female luer connector 10 includes a rigid tubular portion 11, for example, made of plastic, a hollow needle 12, for example, a stainless steel 20 gauge needle fixedly mounted within and relative to the plastic tubular portion 10 and a tubular shield or boot 13 mounted over the needle 12. The tubular shield 13 is made, for example, of rubber, and includes a resilient collapsible tubular portion or sleeve 14 which is concentric to the needle 12 and a septum 15 at the distal end of the collapsible tubular portion 14 which is disposed in facing spaced relation to the needle 12. This construction is similar to that as described in U.S. Pat. No. 5, 122, 123.

Typically, the inside diameter of the plastic tubular portion 11 decreases from about 0.170 inches at the open end to 0.154 inches at a point 0.250 inches in depth from the opening. In addition, due to tolerances, location of the needle 12 and the need to have the needle 12 opened completely when the septum 15 is pushed over the needle 12, the practical thickness allowable for the septum 15 is about 0.100 inches maximum. However, for this thickness, the septum 15 may leak after only two to four punctures.

In order to increase the usable life of the connector and prevent leakage, a rigid ring 16 is disposed about the septum 15 to prevent circumferential distortion of the septum 15. As illustrated, the ring 16 has a flat rectangular shape and is disposed in coextensive relation to the septum 15 while being of an inside diameter less than the relaxed outside diameter of the septum. In this respect, the ring 16 holds the septum under a circumferentially compressive force. For example, where the septum has an outside diameter of 0.125 inches, the ring 16 may have a inside diameter of 0.115 inches so that the septum 15 is circumferentially compressed approximately from 5% to 10%.

It has been found that for a latex rubber septum 15 having a thickness of 0.100 inches, an original outside diameter of 0.125 inches and a compressed diameter of 0.115 inches, the septum will withstand fifty or more punctures by a stainless steel 20 gauge needle when subjected to relatively high pressures. For a septum 15 made of silicone rubber under an initial compression of 10% and a thickness of 0.050 inches, it has been found that such a septum may be pierced over twenty five times with no leakage when subjected to 30 psig air pressure.

Figure 4:
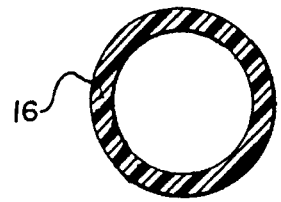
FIG. 4 illustrates a cross sectional view of the compression ring of FIG. 1.

Referring to FIG. 4, the compression ring 16 has an inside diameter of 0.115 inches and a thickness of from 0.015 inches to 0.020 inches. In addition, as indicated in FIG. 1, where the septum 15 has a thickness of 0.100 inches, the ring 16 is coextensive and has a length equal to or slightly greater than the thickness of the septum 15. Further, the septum 15 may be recessed behind the front face of the septum 15 to be hidden from view.

Figure 2:
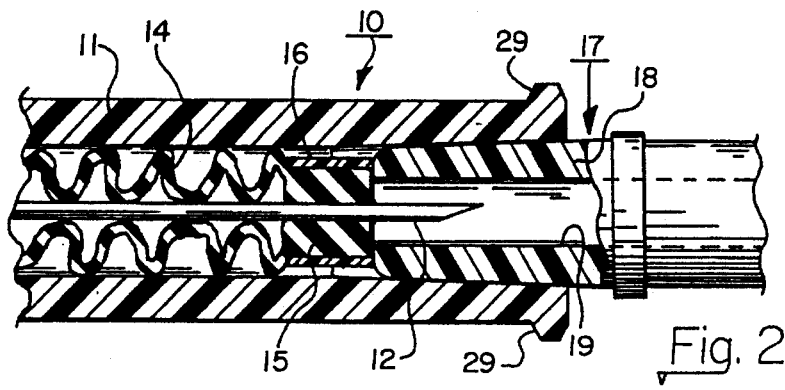
FIG. 2 illustrates a part cross sectional view of the female luer connector of FIG. 1 connected with a male luer connector in accordance with the invention.

Referring to FIG. 2, the female luer connector 10 cooperates with a male luer connector 17 to form a connector assembly. In this respect, the male luer connector 17 includes a hollow tube 18 for movement coaxially into the tubular portion 11 of the female luer connector 10. This tube 18 is sized to abut and move the septum 15 while collapsing the tubular portion 14 of the shield 13 in order to effect piercing of the needle 12 through the septum 15 and entry into the hollow tube 18. In this regard, the hollow tube 18 is provided with a lumen 19 of a size sufficient to receive the needle 12.

As illustrated, the hollow tube 18 may abut the septum 15 as well as the ring 16 when exposed to view.

Typically, the male luer tube 18 penetrates from about 0.250 inches to 0.300 inches into the plastic tubular portion 11 of the female luer connector 10 thereby exposing a length of needle which is sufficient to communicate with the lumen 19 of the male connector 17 to permit conveyance of fluid therebetween. Upon removal of the male connector 17, the collapsed tubular portion 14 of the shield 13 springs forwardly so as to return the septum 15 from the recessed position as shown in FIG. 2 to the extended position of FIG. 1. In this regard, a spring may be used to assist the operation of the collapsible tubular portion 14.

The needle 12 may be a conventional hypodermic needle. However, the needle may also be made of plastic having a pointed or sharp tip.

Once the male connector 17 passes into the female connector 10 to the extent as shown in FIG. 2, communication is made between the lumen 19 of the male connector 17 and the hollow needle 12 for the passage of fluids therebetween. In this regard, the male connector 17 may be made in the form of a male luer connector, a male luer slip, a tubing adaptor, a needle with a shield about the needle and the like. The female luer connector may also be constructed for different purposes.

Figure 3:
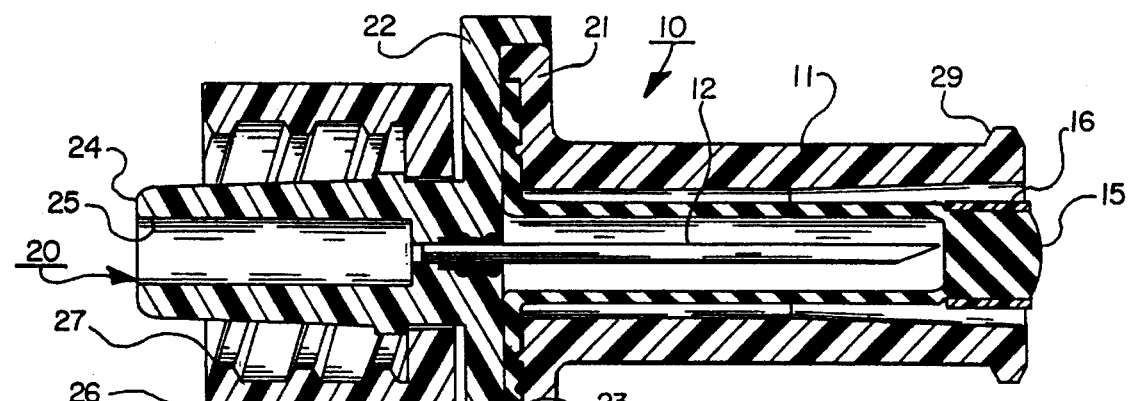
FIG. 3 illustrates a cross sectional view of a female luer connector having a male luer lock at one end in accordance with the invention.

Referring to FIG. 3, wherein like reference characters indicate like parts as above, the female luer connector 10 may be combined with a male luer connector 20 to form a single integrated unit.

As illustrated, the female luer connector 10 has a housing 21 from which the tubular portion 11 extends and which is in the form of a radial flange having an outer diameter to fit within a recessed base 22 of the male luer connector 20. In this respect, the flange 21 may be secured within the base 22 by an ultrasonic seal or in any other suitable fixed relationship. The collapsible tubular portion 14 of the tubular shield 13 is provided with an annular skirt 23 at the base which is compressed and held between the flange 21 of the female luer connector 10 and the base 22 of the male luer connector 20. In this way, the rubber shield 13 is sealed off at the base so as to ensure against leakage between the rubber septum 15 and the outside environment.

The male connector 20 has a tubular nose portion 24 defining a lumen 25 coaxially of the needle 12. As indicated, the needle 12 is fixedly mounted in the base 22.

The male connector 20 also has a lock ring 26 provided with an internal thread 27 concentrically of the nose 24. The lock ring 27 may be fixed to the base 24 so as to receive a tubular portion having an external thread or external projections thereon as is known.

Figure 5:
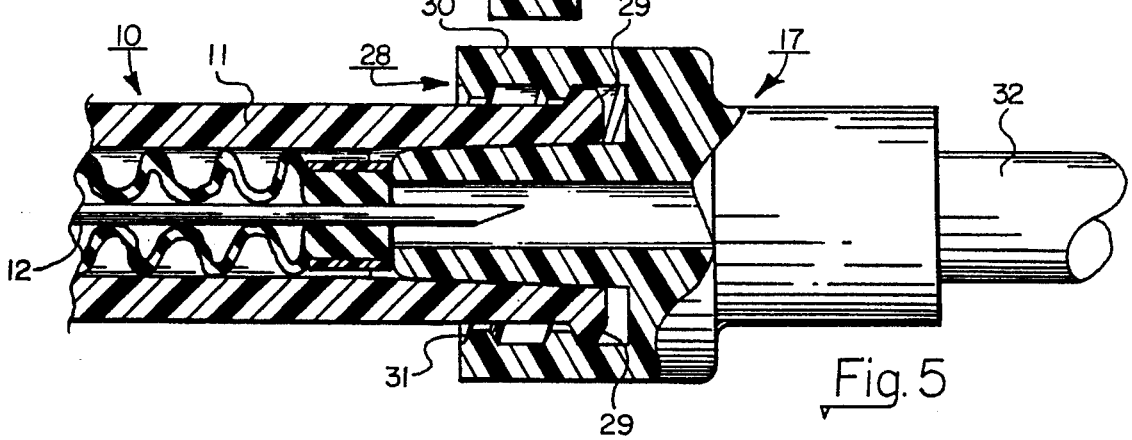
FIG. 5 illustrates a cross sectional view similar to FIG. 2 with a male luer connector releasably connected to a female luer connector in accordance with the invention.

Referring to FIG. 5, wherein like reference characters indicate like parts as above, the connector assembly may be provided with a means 28 for releasably coupling the connectors 10, 17 together. As indicated, this means 28 may include a pair of radially directed projections 29 on the rigid tubular portion 11 of the female connector 10 and a housing 30 on the male connector 17 with an internal thread 31 for threadably receiving the projections 29.

The male connector 17 may also have a tubular portion 32 extending therefrom, for example, for reception of a tubing thereon.

In use, in order to form a connection, the exposed face of the septum 15 of the female connector 10 is wiped with a suitable antiseptic and the male connector 17 is brought into engagement with the septum 15. Continued relative motion between the two connectors 10, 17 causes the septum 15 to be pushed from the extended position of FIG. 1 to the recessed position of FIG. 2 while the needle 12 pierces through the septum 15. At this time, the projections 29 of the female connector 10 have entered into the housing 30 of the male connector 17 so that a twisting of the male and female connector causes the projections 29 to interengage with the internal thread 31 so that the connectors 10, 17 become releasably coupled together against the bias of the compressed rubber sleeve 14.

Unthreading of the connectors 10, 17 relative to each other allows the rubber sleeve 14 to force connectors 10, 17 apart while, at the same time, returning the rubber septum 15 to the extended position sealing off the needle 12 to the surrounding environment. As indicated in FIG. 1, when the septum 15 is in the extended position, the forward face projects slightly from the rigid tubular portion 11 so that the face of the septum 15 may be wiped with a suitable antiseptic prior to again being connected to a male connector.

The male connector 17 may also be made as described in U.S. Pat. No. 5,122,123. In this respect, the tubular portion 18 of the male connector 17 may be provided with a septum at the end which can be pierced by the needle 12 when a connection is made.

Various tests were conducted to evaluate septum leakage using both silicone rubber and latex rubber for the septum at various compression rates after one and twenty five punctures. The compression ring used in the tests was a polycarbonate ring. The degrees of compression used were 0%, 5%, 10% and 20%, each based upon the original outside diameter of the septum. The results of the tests were as follows:

| O.D. | Thickness | Comp. Ring | % Comp. | Result 1X | Result 25X |
|---|---|---|---|---|---|
| SILICONE | | | | | |
| .125 | .050 | .125 | 0 | GD | NG |
| .125 | .050 | .119 | 5 | GD | NG |
| .125 | .050 | .112 | 10 | GD | GD |
| .125 | .050 | .100 | 20 | GD | GD |
| .125 | .100 | .125 | 0 | GD | NG |
| .125 | .100 | .119 | 5 | GD | GD |
| .125 | .100 | .112 | 10 | GD | GD |
| .125 | .100 | .100 | 20 | GD | GD |
| .125 | .125 | .125 | 0 | NG | NG |
| .125 | .125 | .119 | 5 | GD | GD |
| .125 | .125 | .112 | 10 | GD | GD |
| .125 | .125 | .100 | 20 | GD | GD |
| LATEX | | | | | |
| .150 | .050 | .150 | 0 | NG | NG |
| .150 | .050 | .142 | 5 | NG | NG |
| .150 | .050 | .135 | 10 | GD | NG |
| .150 | .050 | .120 | 20 | Septum Deformed | |
| .150 | .100 | .150 | 0 | GD | NG |
| .150 | .100 | .142 | 5 | GD | GD |
| .150 | .100 | .135 | 10 | GD | GD |
| .150 | .100 | .120 | 20 | Septum Deformed | |

Upon completion of this study, the following become evident. First, at the investigated thicknesses, the silicone septums exhibit better leak resistance at all thicknesses and compression rates as compared to latex. In addition, in the case of the silicone septums, even compression as low as 5% has a pronounced effect on leakage in comparison to 0% compression.

The invention thus provides a connector assembly in which a needle which is encased within a collapsible protective shield can be repeatedly pierced through the septum of the shield without a leakage path through the septum being formed under the pressure of an IV line or a vein of a patient.

What is claimed is:

1. A connector assembly comprising a female luer connector including a housing having a rigid tubular portion projecting therefrom, a hollow needle mounted in said housing concentrically within said tubular portion, a tubular shield mounted over said needle and including a resilient collapsible tubular portion concentric to said needle and a septum at a distal end of said collapsible tubular portion in facing relation to said needle and a ring disposed about said septum to circumferentially compress said septum and prevent circumferential distortion of said septum; and a male luer connector including a hollow tube for movement coaxially into said rigid tubular portion of said female luer housing, said hollow tube being sized to abut and move said septum into said rigid tubular portion while collapsing said collapsible tubular portion of said shield to effect piercing of said needle through said septum and entry into said hollow tube.

2. A connector assembly as set forth in claim 1 wherein said female luer has a pair of radially directed projections on an end of said rigid tubular portion and said male luer connector has a housing including an internal thread for receiving said projections to secure said luer connector together.

3. A connector assembly as set forth in claim 1 which further comprises means for releasably coupling said luer connectors together.

4. A connector assembly as set forth in claim 3 wherein said means includes a pair of radially directed projections on said rigid tubular portion and a housing on said male luer connector with an internal thread for threadably receiving said projections.

5. A connector assembly as set forth in claim 1 wherein said ring is made of plastic.

6. A connector assembly as set forth in claim 1 wherein said ring is disposed on said septum to circumferentially compress said septum in an amount sufficient to prevent leakage therethrough under pressure and after repeated punctures.

7. A connector assembly as set forth in claim 1 wherein said septum is partially recessed in said rigid tubular portion and said ring is a flat rectangular ring disposed on said septum and being coextensive of said septum.

8. A connector comprising a housing having a rigid tubular portion projecting therefrom;

a hollow needle mounted in said housing concentrically within said tubular portion;

a tubular shield mounted over said needle and including a resilient collapsible tubular portion concentric to said needle and secured at one end to said housing and a septum at a distal end of said collapsible tubular portion in facing relation to said needle; and a ring disposed about said septum to circumferentially compress said septum and prevent circumferential distortion of said septum in response to repeated passage of said needle through said septum.

9. A connector as set forth in claim 8 which further comprises a pair of projections at one end of said rigid tubular portion to form a releasable locking connection.

10. A connector as set forth in claim 8 wherein said septum has a thin thickness in the range of 0.100 inches and said ring circumferentially compresses said septum.

11. A connector as set forth in claim 8 wherein said ring is a flat rectangular ring disposed on and coextensive with said septum.

12. A connector as set forth in claim 8 wherein said ring has a thickness of from 0.015 to 0.020 inches and an inside diameter of 0.115 inches.

13. A connector assembly comprising a first connector including a rigid tubular portion, a hollow needle fixedly mounted within said tubular portion, a resilient collapsible tubular portion concentric to said needle to define an annular gap therewith, a septum of a thin thickness at a distal end of said collapsible tubular portion in spaced facing relation to said needle and having a surface projecting from said tubular portion, and a rigid compression ring disposed circumferentially of said septum to circumferentially compress said septum; and a second connector including a hollow tube for projecting into said rigid tubular portion of said first connector, said tube having a lumen and being sized to push said septum into said rigid tubular portion to effect piercing of said needle through said septum into said lumen of said hollow tube.

14. A connector assembly as set forth in claim 13 which further comprises means for releasably coupling said connectors together with said hollow tube of said second connector within said tubular portion of said first connector.

15. A connect assembly as set forth in claim 14 wherein said means including a housing on said second connector having a internal thread and a pair of radially directed projections on said rigid tubular portion of said first connector for threading into said internal thread.

16. In combination, a first connector including a rigid tubular portion, a hollow needle fixedly mounted within said tubular portion, a resilient collapsible tubular portion concentrically between said needle and said rigid tubular portion, a cap-shaped septum at a distal end of said collapsible tubular portion for movement between an extended position with a face of said septum at a distal end of said rigid tubular portion and a recessed position within said rigid tubular portion, and a plastic ring disposed circumferentially of said septum to circumferentially compress said septum and prevent circumferential distortion of said septum; and means for moving said septum from said extended position to said recessed position to effect piercing of said needle through said septum while resiliently collapsing said collapsible tubular portion.

17. The combination as set forth in claim 16 wherein said means is a second connector having a hollow tube defining a lumen for receiving said needle with said septum in said recessed position.

18. The combination as set forth in claim 17 which further comprises a housing on said second connector having a internal thread and a pair of radially directed projections on said rigid tubular portion of said first connector for threading into said internal thread.

19. The combination as set forth in claim 16 wherein said ring is disposed on said septum to circumferentially compress said septum in an amount sufficient to prevent leakage therethrough under pressure of 30 psig.

20. The combination as set forth in claim 16 wherein said ring is disposed on said septum to compress said septum in a range of from 5% to 10% of the outside diameter of said septum.

* * * * *